United States Patent [19]

Gruber et al.

[11] Patent Number: 5,446,188
[45] Date of Patent: Aug. 29, 1995

[54] PROCESS FOR THE PRODUCTION OF HIGHLY CONCENTRATED FATTY ALCOHOL SULFATE PASTES

[75] Inventors: Bert Gruber, Bedburg; Hermann Anzinger; Guenter Hendricks, both of Duesseldorf, all of Germany

[73] Assignee: Henkel Kommanditgesellschaft auf Aktien, Duesseldorf, Germany

[21] Appl. No.: 119,159

[22] PCT Filed: Mar. 12, 1992

[86] PCT No.: PCT/EP92/00544

§ 371 Date: Nov. 22, 1993

§ 102(e) Date: Nov. 22, 1993

[87] PCT Pub. No.: WO92/16606

PCT Pub. Date: Oct. 1, 1992

[30] Foreign Application Priority Data

Mar. 21, 1991 [DE] Germany .................. 41 09 250.3

[51] Int. Cl.$^6$ .................. C07C 305/06; C07C 305/14
[52] U.S. Cl. .................. 558/42; 558/41; 558/36
[58] Field of Search .................. 558/42, 41, 36

[56] References Cited

U.S. PATENT DOCUMENTS

| | | |
|---|---|---|
| 2,214,254 | 9/1940 | Mills et al. |
| 3,415,753 | 12/1968 | Stein et al. |
| 3,741,913 | 6/1973 | Waag et al. |
| 4,191,704 | 3/1980 | Mather et al. |
| 4,476,037 | 10/1984 | Ploog et al. |
| 4,495,092 | 1/1985 | Schmid et al. |

FOREIGN PATENT DOCUMENTS

| | | |
|---|---|---|
| 0024711 | 3/1981 | European Pat. Off. |
| 0116905 | 3/1984 | European Pat. Off. |
| 1617160 | 4/1972 | Germany |
| 9102045 | 2/1991 | WIPO |

OTHER PUBLICATIONS

The Journal of the American Oil Chemists' Society vol. 36, May 31, 1959, E. E. Gilbert et al.: "Sulfation with Sulfur Trioxide: Ethenoxylated Long-Chain Alcohols", pp. 208–210.

J. Falbe (ed.), "Surfactants in consumer products", Springer Verlag, Berlin–Heidelberg, 1987, p. 61.

Ind. Eng. Chem. Prod. Res. Develop, 1, 24 (1965).

*Primary Examiner*—Nicky Chan
*Attorney, Agent, or Firm*—Wayne C. Jaeschke; John E. Drach; Henry E. Millson, Jr.

[57] ABSTRACT

A process for the production of a highly concentrated fatty alcohol sulfate paste comprising the steps of: (1) forming a crude sulfonation product by reacting a mixture of an inert gas and sulfur dioxide with a mixture comprised of: (a) an unsaturated fatty alcohol of the formula I $$R^1\text{—OH} \qquad (I)$$

wherein $R^1$ is a linear unsaturated hydrocarbon radical having from 16 to 22 carbon atoms and 1, 2, or 3 double bonds, (b) a saturated fatty alcohol of the formula II $$R^2\text{—OH} \qquad (II)$$

wherein $R^2$ is a linear or branched saturated hydrocarbon radical having from 12 to 22 carbon atoms; wherein the molar ratio of sulfur trioxide/fatty alcohol mixture is from 0.95:1 to 1.3:1 and (2) neutralizing, at a temperature of from 50° C. to 90° C., said crude sulfonation product with a quantity of aqueous base sufficient to form a water-containing fatty alcohol sulfate paste product having a solids content of from 60% to 70% by weight and a viscosity of less than 10 Pa.s at 60° C.

17 Claims, No Drawings

PROCESS FOR THE PRODUCTION OF HIGHLY CONCENTRATED FATTY ALCOHOL SULFATE PASTES

This is a 371 of Pct/EP42/00544 filed Mar. 12, 1992.

BACKGROUND OF THE INVENTION

Field of the Invention

This invention relates to a process for the production of highly concentrated fatty alcohol sulfate pastes by gas sulfonation of fatty alcohol mixtures and subsequent one-step neutralization and hydrolysis.

STATEMENT OF RELATED ART

Anionic surfactants of the fatty alcohol sulfate type, particularly those containing 16 to 18 carbon atoms in the fatty component, show excellent detergent properties and are suitable for the production of laundry detergents, dishwashing detergents and cleaning preparations.

Fatty alcohol sulfates are produced from fatty alcohols which are first converted into the corresponding sulfuric acid semiesters with suitable sulfonating agents, for example gaseous sulfur trioxide, and then neutralized with bases [J. Am. Oil. Chem. Soc. 36, 208 (1960)]. If unsaturated fatty alcohols are used as starting materials, the reaction products have to be subjected to hydrolysis in addition to neutralization in order to prevent, post-acidification. Corresponding processes are described, for example, in Ten. Surf. Det. 15, 299 (1978) and Inc. Eng. Chem. Prod. Res. Develop., 1, 24 (1965).

The use of fatty alcohol sulfates, particularly for the production of powder-form detergents, on an industrial scale has hitherto been limited because even the storage and transport of water-containing fatty alcohol sulfate pastes involve considerable problems. Thus, fatty alcohol sulfate pastes having solids contents of 30 to 70% by weight have such a high viscosity and such a pronounced flow anomaly (rheopexy) at ambient temperature that they are virtually impossible to pack in containers and to circulate by pumping.

A possible solution could be to heat the pastes to a sufficiently high temperature and to make them flowable in this way. However, since fatty alcohol sulfates begin to decompose at temperatures as low as 80° C., storage and handling under these conditions is only possible under the most careful pH control and optionally with additions of alkali.

The alternative approach, namely to reduce the viscosity of fatty alcohol sulfate pastes by dilution with water to such an extent that they can be circulated, is also unfavorable because unnecessary mass transfer in the spray drying of the pastes for the production of powder-form products would involve excessive energy consumption.

In the past, the problem posed by the high viscosity of water-containing anionic surfactant pastes has been the subject of numerous investigations, cf. EP 0 24 711 A1, EP 0 116 905 A1 and DE 16 17 160 which propose the use of alkoxylated alcohols, cumene sulfonate or phosphoric acid esters as viscosity-reducing agents for fatty alcohol sulfate pastes. However, these processes are basically attended by the disadvantage that the incorporation of additives involves additional effort and, in addition, can adversely affect the performance properties of the products.

The problem addressed by the present invention was to provide a process for the production of highly concentrated fatty alcohol sulfate pastes which would be free from the disadvantages mentioned above.

DESCRIPTION OF THE INVENTION

The present invention relates to a process for the production of highly concentrated fatty alcohol sulfate pastes by reaction of fatty alcohols with gaseous sulfur trioxide and subsequent neutralization and hydrolysis, characterized in that mixtures containing a) unsaturated fatty alcohols corresponding to formula (I)

$$R^1OH \qquad (I)$$

in which $R^1$ is a linear unsaturated hydrocarbon radical containing 16 to 22 carbon atoms and 1, 2 or 3 double bonds, and b) saturated fatty alcohols corresponding to formula (II)

$$R^2{-}OH \qquad (II)$$

in which $R^2$ is a linear or branched saturated hydrocarbon radical containing 12 to 22 carbon atoms, are reacted together with a sulfur trioxide/inert gas mixture in a molar ratio of 1:0.95 to 1:1.3 and the reaction products are neutralized in one step carried out at 50° to 90° C. with such a quantity of aqueous base that water-containing fatty alcohol sulfate pastes with a solids content of 60 to 70% by weight (based on the paste), which have a viscosity of less than 10 Pa.s at a temperature of 60° C., are obtained.

It has surprisingly been found that, after sulfonation, neutralization and hydrolysis, mixtures of unsaturated and saturated fatty alcohols have a low viscosity and a low yield point so that the rheopexic flow behavior typical of fatty alcohol sulfates based solely on saturated fatty alcohols is overcome. It is thus possible to produce high-solids fatty alcohol sulfate pastes which are flowable and pumpable, even at low temperatures and at low shear rates.

In addition, the present invention overcomes the hitherto existing prejudice that the neutralization and hydrolysis of acidic sulfonation products based on unsaturated starting materials always has to be carried out in two steps and with a large excess of base. On the contrary, it has been found that these two reactions can be carried out in one step and with equimolar quantities of base (based on the quantity of sulfonating agent used) providing sufficiently high temperatures, for example in the range from 70° to 90° C., are applied.

Typical examples of saturated fatty alcohols corresponding to formula (I), which may be used as component a) in accordance with the invention, are palmitoleyl alcohol, oleyl alcohol, elaidyl alcohol, petroselinyl alcohol, linolyl alcohol, linolenyl alcohol, gadoleyl alcohol or erucyl alcohol. Oleyl alcohol is preferably used.

Saturated fatty alcohols corresponding to formula (II) which are suitable as component b) in accordance with the invention are understood to be, on the one hand, the substantially linear fatty alcohols which are obtained by high-pressure hydrogenation of fatty acid alkyl esters based on natural fats and oils. Typical examples are lauryl alcohol, myristyl alcohol, cetyl alcohol, stearyl alcohol, arachyl alcohol or behenyl alcohol. On the other hand, they also include the partly branched oxoalcohols having C chain lengths in the range mentioned which can be obtained by hydrogenation of the corresponding aldehydes from Roelen's oxo synthesis. Cetyl and/or stearyl alcohol are preferably used.

Components a) and b) may be mixed purely mechanically, for example by stirring, optionally at elevated temperature. The ratio by weight of the unsaturated fatty alcohols to the saturated fatty alcohols may be 99:1 to 50:50 and, more particularly, is in the range from 95:5 to 65:35.

However, technical mixtures directly containing components a) and b) in the ratios by weight indicated are preferably used for the sulfonation reaction. As is known to the expert, the starting materials used for this purpose are normally fats or oils of high iodine value, for example rapeseed oil, sunflower oil, peanut oil, cottonseed oil, coriander oil, soybean oil, linseed oil or beef tallow, which are first converted into the methyl esters and subsequently hydrogenated to the alcohols with the double bonds of their unsaturated components intact.

The sulfonation of the fatty alcohol mixtures containing components a) and b) with gaseous sulfur trioxide may be carried out by the method known for fatty acid lower alkyl esters [J. Falbe (ed.), "Surfactants in Consumer Products", Springer Verlag, Berlin-Heidelberg, 1987, page 61], continuous reactors operating on the falling-film principle preferably being used. The sulfur trioxide is diluted with an inert gas, preferably air or nitrogen, and used in the form of a gas mixture containing the sulfonating agent in a concentration of 1 to 8% by volume and, more particularly, 2 to 5% by volume.

The gaseous sulfur trioxide is used in a ratio of 0.95 to 1.3 mol and preferably 1.05 to 1.1 mol sulfur trioxide to 1 mol fatty alcohol. The sulfonation reaction may be carried out at temperatures $T^1$ of 25° to 70° C., but is preferably carried out at temperatures in the range from 30° to 50° C.

The acidic sulfonation products formed during the sulfonation are stirred into aqueous bases, neutralized and at the same time hydrolyzed in order to prevent post-acidification of the compounds. The neutralization/hydrolysis step may be carried out at temperatures of 70° to 90° C. The sultones formed are partly hydrolyzed to form sulfonates without elimination of the sulfate group. In one preferred embodiment of the process according to the invention, the acidic sulfonation products are neutralized immediately on leaving the reactor, i.e. without further cooling, so that they are simultaneously hydrolyzed.

Suitable neutralization bases are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and also primary, secondary or tertiary $C_{1-4}$ alkyl amines. The neutralization bases are preferably used in the form of 20 to 50% by weight aqueous solutions, aqueous sodium hydroxide solutions being preferred.

The sulfonation product is a mixture which essentially contains alkyl and alkenyl sulfates. Since addition of the sulfur trioxide onto the double bond also takes place where unsaturated fatty alcohols are used for the sulfonation reaction, the mixture also contains substances which have an internal sulfonate group or a sulfonate group and a sulfate group. The percentage content of these internal sulfonation products is typically in the range from 10 to 25% by weight, based on the quantity of anionic surfactant. It may well be that the unexpected effect of the favorable rheological behavior is linked to the presence of internal sulfonation products in the quantities mentioned.

After neutralization, the sulfonation products may be bleached in known manner by addition of hydrogen peroxide or sodium hypochlorite solution. Based on the solids content in the solution of sulfonation products, quantities of 0.2 to 2% by weight hydrogen peroxide, expressed as 100% substance, or corresponding quantities of sodium hypochlorite are used for this purpose. The pH value of the solutions may be adjusted to values of 7.5 to 10 by addition of alkali. In addition, it is advisable to add preservatives, for example formaldehyde solution, p-hydroxybenzoate, sorbic acid or other known preservatives, for stabilization against bacterial contamination.

The highly concentrated fatty alcohol sulfate pastes obtainable by the process according to the invention have excellent detergent properties and show high solubility in cold water. Accordingly, they are suitable for the production of powder-form or liquid laundry detergents, dishwashing detergents and cleaning products and hair-care and personal hygiene products, in which they may be present in quantities of 1 to 25% by weight, based on the solids content of the particular product.

The following Examples are intended to illustrate the invention without limiting it in any way.

EXAMPLES

I PRODUCTION EXAMPLES

EXAMPLE 1

260 g (1 mol) of a technical oleyl/cetyl alcohol (HD Ocenol ® 50–55, a product of Henkel KGaA), which has the following composition: myristyl alcohol 5% by weight, cetyl alcohol 30% by weight, oleyl alcohol 65% by weight; iodine value 53, hydroxyl value 215, were introduced into a 1 liter sulfonation reactor equipped with jacket cooling and a gas inlet pipe and reacted with 84 g (1.05 mol) sulfur trioxide at $T^1=45°$ C. The sulfur trioxide was driven out by heating from a corresponding quantity of 65% by weight oleum, diluted with nitrogen to a concentration of 5% by volume and introduced into the starting product in 30 minutes. The crude sulfonation product was then neutralized and, at the same time, hydrolyzed with 214 g of a 20% by weight aqueous sodium hydroxide solution at a temperature $T^2$ of 80° C. The reaction product was then adjusted to a pH value of 10 with sodium hydroxide.

| Characteristic data of the product: | |
| --- | --- |
| Anionic surfactant content | 65.4% by weight |
| Sulfate content | 53.1% by weight |
| Sulfonate content | 12.3% by weight |
| Unsulfonated components | 2.3% by weight |
| Sodium sulfate | 1.4% by weight |
| Water | 30.9% by weight |

The anionic surfactant content and the unsulfonated components were determined by the DGF Standard Methods (DGF-Einheitsmethoden, Stuttgart, 1950–1984, H-III-10 and G-II-6b). The sodium content was calculated as sodium sulfate while the water content was determined by the Fischer method.

EXAMPLE 2

In a continuous falling-film reactor (length 120 cm, cross-section 1 cm, educt throughput 600 g/h) equipped with jacket cooling and a side inlet for $SO_3$ gas, 2600 g (10 mol) of a technical oleyl alcohol (HD Ocenol® 90-95, a product of Henkel KGaA) having the following composition: myristyl alcohol 1% by weight, cetyl alcohol 5% by weight, oleyl alcohol 94% by weight; iodine value 93, hydroxyl value 210, were reacted at 50° C. with 880 g (11 mol) gaseous sulfur trioxide. The acidic reaction mixture was continuously introduced into 50% by weight sodium hydroxide solution at $T^2 = 80°$ C. and then neutralized and hydrolyzed at the same time.

| Characteristic data of the product: | |
|---|---|
| Anionic surfactant content | 69.3% by weight |
| Sulfate content | 57.7% by weight |
| Sulfonate content | 11.6% by weight |
| Unsulfonated components | 2.2% by weight |
| Sodium sulfate | 1.2% by weight |
| Water | 27.3% by weight |

EXAMPLE 3

In a Ballestra 4-tube reactor (length 12 m, raw material throughput 100 kg/h), 4000 kg of a technical oleyl/cetyl alcohol (HD-Ocenol 50/55, Henkel KGaA) were reacted with a sulfur trioxide/air mixture (5% by volume $SO_3$, flow rate 179 m³/h), the quantity of sulfonating agent being gauged in such a way that an acid value of 160 to 164 was established in the acidic reaction product throughout the entire reaction. The alcohol was introduced into the reactor at a temperature of 45° C., the temperature of the $SO_3$/air mixture was 27° C. and the temperature of the reactor cooling water was 40° to 45° C. After leaving the reactor, the acidic sulfonation product, which had a temperature of 50° C., was neutralized and hydrolyzed at $T^2 = 70°$ C. with such a quantity of 50% by weight sodium hydroxide that a solids concentration in the paste of 73.2% was obtained.

The end reaction product was adjusted to pH 10 and was bleached with 1% by weight, based on the solids content, of a 13% by weight aqueous solution of sodium hypochlorite.

| Characteristic data of the product: | |
|---|---|
| Anionic surfactant content | 66.6% by weight |
| Sulfate content | 52.6% by weight |
| Sulfonate content | 14.0% by weight |
| Unsulfonated components | 3.2% by weight |
| Sodium sulfate | 2.3% by weight |
| Water | 27.9% by weight |

II. DETERMINATION OF YIELD POINT AND VISCOSITY

Examples 4 to 8, Comparison Example C1

The rheological measurements were performed with a Carri-Med CS 100 shear-stress-controlled rotational rheometer with a plate/plate measuring system at temperatures in the range from 20° to 80° C. The results are set out in Tables 1 and 2.

TABLE 1

| | | Yield points (in Pa) | | |
|---|---|---|---|---|
| | Fatty alcohol sulfate | Temperature (°C.) | | |
| Ex. | paste | 20 | 40 | 60 |
| 4 | Acc. to Ex. 3 | 105 | 48 | 7 |
| C1 | Sulfopon ® T | — | — | 63 |

TABLE 2

| | | Viscosity (in Pa.s) | | |
|---|---|---|---|---|
| | Fatty alcohol sulfate | T | Shear rate | |
| Ex. | paste | °C. | 10/s | 30/s | 50/s |
| 5 | Acc. to Example 3 | 20 | 54 | 21 | 14 |
| 6 | Acc. to Example 3 | 40 | 32 | 14 | 10 |
| 7 | Acc. to Example 3 | 60 | 6 | 5 | 4 |
| 8 | Acc. to Example 3 | 80 | 3 | 2 | 1 |

Sulfopon ® T:

Fatty alcohol sulfate paste based on saturated $C_{16/18}$ tallow fatty alcohol (a product of Henkel KGaA). The yield points at 20° to 40° C. could not be measured for this paste. In addition, the paste could not flow below 60° C.

What is claimed is:

1. A process for the production of a highly concentrated fatty alcohol sulfate paste comprising the steps of: (1) forming a crude sulfonation product by reacting a mixture of an inert gas and sulfur trioxide with a mixture comprised of: (a) an unsaturated fatty alcohol of the formula I $$R^1-OH \qquad (I)$$

wherein $R^1$ is a linear unsaturated hydrocarbon radical having from 16 to 22 carbon atoms and 1, 2 or 3 double bonds, (b) a saturated fatty alcohol of the formula II $$R^2-OH \qquad (II)$$

wherein $R^2$ is a linear or branched saturated hydrocarbon radical having from 12 to 22 carbon atoms; wherein the molar ratio of sulfur trioxide/fatty alcohol mixture is from 0.95:1 to 1.3:1; (2) neutralizing in one step, at a temperature of from 50° C. to 90° C., said crude sulfonation product with a quantity of aqueous base sufficient to form a water-containing fatty alcohol sulfate paste product having a solids content of from 60% to 70% by weight and a viscosity of less than 10 Pa.s at 60° C.

2. The process of claim 1 wherein said unsaturated fatty alcohol is oleyl alcohol.

3. The process of claim 1 wherein said saturated fatty alcohol is cetyl alcohol or stearyl alcohol.

4. The process of claim 1 wherein the weight ratio of said unsaturated fatty alcohol of formula (I) to said saturated fatty alcohol of formula (II) is from 99:1 to 50:50.

5. The process of claim 1 wherein step (1) is carried out at a temperature of from 25° to 70° C.

6. The process of claim 1 wherein in step (1) the sulfur trioxide is present in said inert gas mixture in from 1 to 8% by volume sulfur trioxide.

7. The process of claim 1 wherein step (1) is carried out in a continuous falling-film reactor.

8. The process of claim 1 wherein said aqueous base in step (2) is a 20% to 50% by weight aqueous solution of an alkali metal hydroxide.

9. The process of claim 1 wherein the temperature in step (2) is from 70° C. to 90° C., 10. The process of claim 1 wherein in step (1) the molar ratio of sulfur trioxide to fatty alcohol mixture is from 1.05:1 to 1.1:1.

11. The process of claim 5 wherein step (1) is carried out at a temperature of from 30° C. to 50° C.

12. The process of claim 6 wherein the sulfur trioxide is present in the inert gas mixture at a concentration of from 2 to 5% by volume.

13. The process of claim 1 wherein the weight ratio of said unsaturated fatty alcohol of formula (I) to said saturated fatty alcohol of formula (II) is from 99:1 to 50:50; step (1) is carried out at temperature of from 25° C. to 70° C.; in step (1) the molar ratio of sulfur trioxide to fatty alcohol mixture is from 1:05:1 to 1.1:1; and the temperature in step (2) is from 70° C. to 90° C.

14. The process of claim 13 wherein step (1) is carried out at a temperature of from 30° C. to 50° C.

15. The process of claim 13 wherein step (1) is carried out in a continuous falling-film reactor.

16. The process of claim 13 wherein said unsaturated fatty alcohol is oleyl alcohol, and said saturated fatty alcohol is cetyl alcohol or stearyl alcohol.

17. The process of claim 1 wherein the weight ratio of said unsaturated fatty alcohol of formula (I) to said saturated fatty alcohol of formula (II) is from 95:5 to 65:35.

* * * * *